US005563122A

United States Patent [19]

Endo et al.

[11] Patent Number: 5,563,122
[45] Date of Patent: Oct. 8, 1996

[54] STABILIZED PARATHYROID HORMONE COMPOSITION

[75] Inventors: Ken Endo; Shinji Sato; Yoshinori Sugiyama; Masaru Ohno; Hideo Sakakibara, all of Shizuoka, Japan

[73] Assignee: Asahi Kasei Kogyo Kabushiki Kaisha, Osaka, Japan

[21] Appl. No.: 244,758

[22] PCT Filed: Dec. 8, 1992

[86] PCT No.: PCT/JP92/01599

§ 371 Date: Sep. 26, 1994

§ 102(e) Date: Sep. 26, 1994

[87] PCT Pub. No.: WO92/01599

PCT Pub. Date: Jun. 24, 1993

[30] Foreign Application Priority Data

Dec. 9, 1991 [JP] Japan ................................... 3-350236
Nov. 24, 1992 [JP] Japan ................................... 4-313381

[51] Int. Cl.⁶ ........................... A61K 38/29; A61K 47/02; A61K 47/26
[52] U.S. Cl. ................ 514/12; 514/21; 514/769; 514/777; 514/970; 530/344
[58] Field of Search ......................... 530/324, 344, 530/427; 514/12, 21, 970, 769, 777

[56] References Cited

U.S. PATENT DOCUMENTS

| 4,806,343 | 2/1989 | Carpenter et al. | 514/777 |
| 5,344,644 | 9/1994 | Igari et al. | 514/12 |
| 5,496,801 | 3/1996 | Holthuis et al. | 514/2 |

FOREIGN PATENT DOCUMENTS

| 499990 | 8/1992 | European Pat. Off. | 530/324 |
| 60940 | 3/1988 | Japan . | |
| 22233 | 1/1990 | Japan . | |
| 41033 | 2/1991 | Japan . | |
| 247034 | 9/1992 | Japan . | |

OTHER PUBLICATIONS

Halsted, ed, "The Laboratory In Clinical Medicine", published 1976 by W. P. Saunders Co. (Phil.), pp. 792–796.
Archives of Pathology & Laboratory Medicine, vol. 110, issued Jul. 1986, Klee et al, "CAP Survey of Parathyroid Hormone Assays", pp. 588–591.

*Primary Examiner*—Jeffrey E. Russel
*Attorney, Agent, or Firm*—Pennie & Edmonds

[57] ABSTRACT

A safe, stabilized lyophilized preparation comprising parathyroid hormone (PTH) as an active ingredient and effective amounts of sugar and sodium chloride to provide a stable preparation of parathyroid hormone.

28 Claims, No Drawings

STABILIZED PARATHYROID HORMONE COMPOSITION

FIELD OF INVENTION

The present invention relates to a method of stabilizing parathyroid hormone (hereinafter generally designated as PTH) and compositions containing parathyroid hormone as the active ingredient.

1. PRIOR ART

PTH is a hormone which has activity, similar to calcitonin and vitamin D, in controlling serum calcium levels, and which can be used as a diagnostic reagent for hypoparathyroidism. Generally a sugar such as mannitol or polymer substance such as gelatin is added to a lyophilized preparation of an injectable solution containing trace amount of PTH. (Japanese Patent applications No. 63-60940 and No. 2-111)

2. PROBLEMS TO BE SOLVED BY THE INVENTION

Mannitol is the conventional stabilizing agent used in lyophilized preparations of peptides or proteins for injectable solutions. However, when mannitol is used as a stabilizing agent for lyophilized preparations of PTH used for injectable solutions, its stabilizing effect is unsatisfactory. Polymer substances, such as gelatin, give high stabilizing effects, however its immunological safety is still uncertain.

3. MEANS FOR SOLVING PROBLEMS

During continuing studies to find a stable preparation of PTH, it was unexpectedly discovered that dramatically improved stability for lyophilized preparations of PTH can be obtained by combining a constant amount of sodium chloride with a sugar together before lyophilization, as compared with the use of a sugar alone.

As a result, excellent heat stable lyophilized preparations of PTH can be prepared using a combination of sugar and sodium chloride as stabilizing agents.

An object of the present invention is to provide a lyophilized preparation of PTH containing PTH as the active ingredient and effective amounts of a sugar and sodium chloride as the stabilizing agents.

Another object of the present invention is to provide a method of stabilizing a preparation of PTH comprising dissolving PTH, together with effective amounts of a sugar and sodium chloride in an aqueous medium, and lyophilizing the same.

As an active ingredient PTH is a peptide possessing the activity of increasing serum calcium. PTH has a molecular weight of approx. 4,000–10,000, and consists of an amino acid sequence of 34–84 amino acids for natural PTH or its analogues. Examples thereof are; human PTH(h-PTH)(1-84)[Biochemistry, 17, 5723 (1978)]; h-PTH(1-38) (Japanese Patent Unexamined Publication No. 57-81448); h-PTH(1-34)[Hoppe Seyler's Z. Physiol. Chem., 355, 415 (1974)]; h-PTH(1-34)NH$_2$, (Japanese Patent Unexamined Publication No. 58-96052); [Nle$^8$, $^{18}$]h-PTH(1-34); [Nle$^8$, $^{18}$, Tyr$^{34}$]h-PTH(1-34) (ibid., No.55-113753); [Nle$^8$, $^{18}$]h-PTH(1-34)NH$_2$(ibid., No.61-24598); [Nle$^8$, $^{18}$,Tyr$^{34}$]h-PTH(1-34)NH$_2$(ibid., No.60-24996); rat-PTH(1-84) [*J. Biol. Chem.*, 259(5), 3320 (1984) ]; rat-PTH(1-34) [*Endocrinol.*, 117 (3) , 1230(1985)]; bovine-PTH(1-84)[*Am. J. Med.*, 50, 639(1971)]; bovine -PTH(1-34); and, bovine-PTH(1-34)NH$_2$[Phytho biology Annual, 11, 53 (1981)].

A preferred example of PTH is h-PTH(1-34) having a molecular weight of approx. 4,400, with an amino acid sequence of 34 amino acids.

Examples of sugar in the present invention are, preferably a monosaccharide or disaccharide. Examples of monosaccharides are mannitol, glucose, sorbitol or inositol, and among these mannitol is the most preferred. Examples of disaccharides are sucrose, maltose, lactose and trehalose. These disaccharides can be used alone or in combination with other sugars. The most preferred examples of disaccharides are sucrose, maltose and lactose.

The amount of sugar to be added is preferably greater than one weight part of sugar per weight part of PTH. It is preferred to use from 50–1,000 weight parts of sugar per weight part of PTH.

The larger the amount of sodium chloride to be added to that of sugar, the more stable the PTH preparation will be. However, when the amount of sodium chloride exceeds 20% of the weight of sugar, a lyophilized cake of the preparation will suffer shrinkage and the stability tends to decrease. Thus, the amount of sodium chloride to be added can be from about $1/1,000$ weight part to $1/5$ weight part per weight part of sugar, preferably from about $1/100$–$1/10$ weight part thereof.

Examples of aqueous medium which can be used in the present invention are distilled water for injection and physiological saline or buffer solutions. Water soluble organic solvents such as nontoxic amounts of ethanol can also be added to such aqueous medium.

The lyophilized composition of the present invention, can be prepared by, for example, mixing PTH, sugar and sodium chloride, and, if required, known pH adjusters, isotonicity agents, stabilizing agents, excipients and antiseptic agents. The mixture can be dissolved in an aqueous medium, and, after aseptic filtration, lyophilized using conventional methods. Tray or vial lyophilization may be accomplished using known conditions.

The thus prepared lyophilized composition can be formulated into dosage forms containing, for example, 1 µg–150 µg of PTH. The dosage form will preferably comprise PTH, such as h-PTH(1–34), in an injectable lyophilized preparation.

EXAMPLES

The following examples illustrate the present invention but should not be construed as limiting the present invention.

EXAMPLE 1

2.16mg of h-PTH(1–34) (Asahi Chemical Industry Co.) 300 mg of mannitol and 30 mg of sodium chloride were dissolved in 30ml of sterile distilled water. After aseptic filtration, the resulting solution was broken up into 0.5 ml samples and poured into glass vials. The samples were lyophilized, and placed in a nitrogen atmosphere. A stopper was then fully inserted into each glass vial. An aluminum seal was then added to each vial to prepare a lyophilized preparation for use as an injectable solution. (hereinafter designated as preparation 1)

EXAMPLE 2

Eight lyophilized preparations were made in the same manner as used for preparation 1, except that the mannitol used in preparation 1 was replaced with the sugars indicated in table 1. Also, the sugar and sodium chloride were used in the amounts shown in Table 1.

TABLE 1

| The Preparation | Sugar | | Sodium Chloride |
| --- | --- | --- | --- |
| 2 | sucrose | 300 mg | 30 mg |
| 3 | sucrose | 300 mg | 30 mg |
| 4 | sucrose | 300 mg | 60 mg |
| 5 | sucrose | 600 mg | 60 mg |
| 6 | sucrose | 300 mg | 30 mg |
| 7 | maltose | 300 mg | 30 mg |
| 8 | sucrose | 600 mg | 30 mg |
| 9 | mannitol | 600 mg | 30 mg |

EXAMPLE 3

0.3mg of bovine PTH(1–34) (Sigma corp.) 240 mg of mannitol and 24 mg of sodium chloride were dissolved in 12 ml of sterile distilled water. After aseptic filtration, the resulting solution was broken up into 0.5 ml samples and poured into glass vials. The samples were lyophilized and fuse-sealed to prepare lyophilized preparations for use as injectable solutions.

EXAMPLE 4

0.2mg of Rat PTH(1–34)( Ind. Co.), 160 mg of trehalose and 10 mg of sodium chloride were dissolved in 8 ml of sterile distilled water. The resulting solution was broken up into 0.1 ml samples and poured into glass vials. The samples were lyophilized and fuse-sealed to prepare a reference standard for measuring content.

EXAMPLE 5

0.6 mg of [$Nle^8, {}^{18}$]h-PTH(1–34) (Asahi Chemical Industry Co.), 160 mg of trehalose and 24 mg of sodium chloride were dissolved in 24 ml of sterile distilled water. After aseptic filtration, the resulting solution was broken up into 0.5 ml samples and poured into glass vials. The samples were lyophilized and a stopper was inserted into each glass vial. The aluminum seal was then added to each vial to prepare a lyophilized preparation for use as an injectable solution.

EXAMPLE 6

0.15 mg of h-PTH(1–84) (Signa Corp.), 100 mg of trehalose and 10 mg of sodium chloride were dissolved in 10 ml of sterile distilled water. The resulting solution was broken up into 0.2 ml samples and poured into glass vials. The samples were lyophilized and fuse-sealed to prepare a reference standard for assaying biological activity.

EXAMPLE 7

0.54 mg of h-PTH(1–34) (Asahi Chemical Industry Co.), 75 mg of glucose and 7.5 mg of sodium chloride were dissolved in 15 mls of sterile distilled water. After aseptic filtration, the resulting solution was broken up into 1 ml samples and poured into glass vials. The samples were lyophilized and a stopper was inserted and each glass vial. An aluminum seal was the added to each vial to prepare a lyophilized preparation to be used as an injectable solution.

EXAMPLE 8

1.08 mg of h-PTH(1–34) (Asahi Chemical Industry Co.), 300 mg of sorbitol and 15 mg of sodium chloride were dissolved in 15 ml of sterile distilled voter. After aseptic filtration, the resulting solutions were broken up into 0.5 ml samples and poured into glass vials. The samples were lyophilized. A stopper was then inserted into each glass vial to prepare a lyophilized preparation for use as an injectable solution.

EXAMPLE 9

1.08 mg of h-PTH(1–34) (Asahi Chemical Industry Co.), 300 mg of inositol and 30mg of sodium chloride were dissolved in 15 ml of sterile distilled water. After aseptic filtration, the resulting solution was broken up into 0.5 ml samples and poured into glass vials. The samples were lyophilized and a stopper was inserted into each glass vial. An aluminum seal was then added to each vial to prepare a lyophilized preparation for use as an injectable solution.

EXAMPLE 10

Stability test for PTH:

[Test materials]

Preparations 1–9, obtained in Examples 1 and 2, and control preparations 1–7, herein described below were used in stability tests.

[Preparing the control preparation]

(1) 2.16 mg of h-PTH(1–34) (Asahi Chemical Industry Co.) 30 mg of sodium chloride were dissolved in 30 ml of sterile distilled water. After aseptic filtration, the resulting solution was broken up into 0.5 ml samples and poured into glass vials. The samples were lyophilized, and placed in a nitrogen atmosphere. A stopper was then inserted into each glass vial. An aluminum seal was then added to each vial to prepare a lyophilized preparation for use as an injectable solution. (control preparation 1)

(2) 2.16 mg of h-PTH(I-34) (Asahi Chemical Industry Co.) and 300 mg of mannitol were used to prepare a preparation to be used as an injectable solution in the same manner as control preparation 1.

(Control Preparation 2)

(3) 2.16 mg of h-PTH(1–34) (Asahi Chemical Industry Co.) and 300 mg of sucrose were used to prepare a preparation to be used as an injectable solution in the same manner as control preparation 1.

(control preparation 3)

(4) 2.16 mg of h-PTH(I-34) (Asahi Chemical Industry Co.) and 300 mg of maltose were used to prepare a preparation to be used as an injectable solution in the same manner as control preparation 1.

(Control Preparation 4)

(5) 2.16 mg of h-PTH(1–34) (Asahi Chemical Industry Co.) and 300 mg of lactose were used to prepare a preparation to be used as an injectable solution in the same manner as control preparation 1.

(Control Preparation 5)

(6) 2.16mg of h-PTH(1–34) (Asahi Chemical Industry Co.) and 600 mg of sucrose were used to prepare a preparation to be used as an injectable solution in the same manner as control preparation 1.

(Control Preparation 6)

(7) 2.16 mg of h-PTH(I-34) (Asahi Chemical Industry Co.) and 600 mg of mannitol were used to prepare a preparation to be used as an injectable solution in the same manner as control preparation 1.

(Control Preparation 7)

[Test method]

Preparations 1–9 obtained in Examples 1 and 2, and control preparations 1–7 were stored at 40° C. Each sample was collected at constant time and PTH content as measured using high performance liquid chromatography (HPLC) under the following conditions.

HPLC measuring conditions:

Column: YMC AM-303 ODS S-5 120A (YMC Co.) inner diameter 4.6×250 mm

Mobile phase: 0.1% TFA: acetonitrile=73:27–68:32(17 min.)

Flow rate: 1.0 ml/min.

Detection: UV 280 nm

[Test result]

Compositions of each sample together with residual rates of PTH over 3 months at 40° C. are shown in Table 2.

TABLE 2

| Sample | Sugar | Amount Added* | Sodium chloride | PTH residual rate (%) at 40° C. | | | |
|---|---|---|---|---|---|---|---|
| | | | | initial | 1M** | 2M | 3M |
| control 1 | no add. | | 0.5 mg | 100 | 86 | 82 | 75 |
| control 2 | mannitol | 5 mg | no addition | 100 | 89 | 84 | 76 |
| preparation 1 | mannitol | 5 mg | 0.5 mg | 100 | 94 | 93 | 91 |
| control 3 | sucrose | 5 mg | no addition | 100 | 90 | 85 | 74 |
| preparation 2 | sucrose | 5 mg | 0.1 mg | 100 | 95 | 93 | 90 |
| preparation 3 | sucrose | 5 mg | 0.5 mg | 100 | 98 | 95 | 93 |
| preparation 4 | sucrose | 5 mg | 1.0 mg | 100 | 96 | 93 | 90 |
| preparation 5 | sucrose | 10 mg | 1.0 mg | 100 | 99 | 97 | 95 |
| control 4 | maltose | 5 mg | no addition | 100 | 84 | 79 | 73 |
| preparation 6 | maltose | 5 mg | 0.5 mg | 100 | 95 | 94 | 92 |
| control 5 | lactose | 5 mg | no addition | 100 | 83 | 80 | 74 |
| preparation 7 | lactose | 5 mg | 0.5 mg | 100 | 94 | 92 | 91 |
| control 6 | sucrose | 10 mg | no addition | 100 | 89 | 84 | 79 |
| preparation 8 | sucrose | 10 mg | 0.5 mg | 100 | 98 | 96 | 96 |
| control 7 | mannitol | 10 mg | no addition | 100 | 86 | 82 | 75 |
| preparation 9 | mannitol | 10 mg | 0.5 mg | 100 | 91 | 90 | 89 |

*amount added is shown by a conversion of numerical value per vial.
**month

As shown in Table 2, preparations according to the present invention which contain combinations of sodium chloride and sugar are more stable than control preparations which contain sodium chloride alone or sugar alone. Thus, the effect of combinations of sodium chloride and sugar was confirmed. The addition of sugar alone reveals inferior stability after 3 month storage at 40° C.

The further addition of sodium chloride alone shows disadvantages such as shrinkage of the lyophilized cake and decreased stability.

EFFECT OF THE INVENTION

As illustrated, a safe, stabilized lyophilized preparation of a parathyroid hormone (PTH) containing PTH as an active ingredient together with stabilizing amounts of a sugar and sodium chloride can be obtained.

We claim:

1. A lyophilized composition comprising a parathyroid hormone in an amount 1 μg–150 μg per composition, a sugar and sodium chloride, wherein said sugar and sodium chloride are present in sufficient amounts to stabilize said parathyroid hormone within the lyophilized composition.

2. The composition according to claim 1 wherein the sugar is a monosaccharide or a disaccharide.

3. The composition according to claim 2 wherein the monosaccharide is mannitol.

4. The composition according to claim 2 wherein the monosaccharide is glucose.

5. The composition according to claim 2 wherein the monosaccharide is sorbitol.

6. The composition according to claim 2 wherein the monosaccharide is inositol.

7. The composition according to claim 2 wherein the disaccharide is sucrose.

8. The composition according to claim 2 wherein the disaccharide is maltose.

9. The composition according to claim 2 wherein the disaccharide is lactose.

10. The composition according to claim 2 wherein the disaccharide is trehalose.

11. A method for preparing a stabilized lyophilized parathyroid hormone composition, which method comprises:

i) forming a mixture by dissolving in an aqueous medium a parathyroid hormone in an amount 1 μg–150 μg per composition, a sugar and sodium chloride, wherein said sugar and sodium chloride are present in sufficient amounts to stabilize said parathyroid hormone within the lyophilized composition; and ii) lyophilizing the mixture.

12. The method according to claim 11 wherein the sugar is a monosaccharide or a disaccharide.

13. The method according to claim 12 wherein the monosaccharide is mannitol.

14. The method according to claim 12 wherein the monosaccharide is glucose.

15. The method according to claim 12 wherein the monosaccharide is sorbitol.

16. The method according to claim 12 wherein the monosaccharide is inositol.

17. The method according to claim 12 wherein the disaccharide is sucrose.

18. The method according to claim 12 wherein the disaccharide is maltose.

19. The method according to claim 12 wherein the disaccharide is lactose.

20. A lyophilized composition comprising a parathyroid hormone, sodium chloride, and a sugar selected from the group consisting of sorbitol, inositol, sucrose, maltose, lactose, mannitol and trehalose, wherein said sugar and sodium chloride are present in sufficient amounts to stabilize said parathyroid hormone within said lyophilized composition.

21. A method for preparing a stabilized, lyophilized parathyroid hormone composition, which method comprises:

forming a mixture by dissolving in an aqueous medium a parathyroid hormone, a sugar and sodium chloride, wherein
 a) said sugar and sodium chloride are present in sufficient amounts to stabilize said parathyroid hormone within the lyophilized composition; and
 b) said sugar is a monosaccharide or a disaccharide selected from the group consisting of mannitol, sorbitol, inositol, sucrose, maltose, lactose and trehalose; and ii) lyophilizing the mixture.

22. The method according to claim 21 wherein said sugar is mannitol.

23. The method according to claim 21 wherein said sugar is sorbitol.

24. The method according to claim 21 wherein said sugar is inositol.

25. The method according to claim 21 wherein said sugar is sucrose.

26. The method according to claim 21 wherein said sugar is maltose.

27. The method according to claim 21 wherein said sugar is lactose.

28. The method according to claim 21 wherein said sugar is trehalose.

* * * * *